(12) United States Patent
Alpini et al.

(10) Patent No.: US 8,585,640 B2
(45) Date of Patent: *Nov. 19, 2013

(54) NON-SHORTENING HIGH ANGLE WRAPPED BALLOONS

(75) Inventors: Alfred A. Alpini, Landenberg, PA (US); Michael Houghton, Newark, DE (US); Kenneth Newcomb, Wilmington, DE (US); Jeffrey Towler, Wilmington, DE (US)

(73) Assignee: W.L. Gore & Associates, Inc., Newark, DE (US)

(*) Notice: Subject to any disclaimer, the term of this patent is extended or adjusted under 35 U.S.C. 154(b) by 177 days.

This patent is subject to a terminal disclaimer.

(21) Appl. No.: 12/824,343

(22) Filed: Jun. 28, 2010

(65) Prior Publication Data

US 2010/0262178 A1    Oct. 14, 2010

Related U.S. Application Data

(63) Continuation of application No. 11/501,190, filed on Aug. 7, 2006, now Pat. No. 7,785,290.

(51) Int. Cl.
*A61M 31/00* (2006.01)

(52) U.S. Cl.
USPC .................................................. 604/96.01

(58) Field of Classification Search
USPC ............................................... 604/96.01
See application file for complete search history.

(56) References Cited

U.S. PATENT DOCUMENTS

| | | | |
|---|---|---|---|
| 1,690,995 A | 11/1928 | Pratt |
| 3,640,282 A | 2/1972 | Kamen |
| 3,746,003 A | 7/1973 | Blake et al. |
| 3,953,566 A | 4/1976 | Gore |
| 4,003,382 A | 1/1977 | Dyke |
| 4,106,509 A | 8/1978 | McWhorter |
| 4,187,390 A | 2/1980 | Gore |
| 4,194,041 A | 3/1980 | Gore et al. |
| 4,279,245 A | 7/1981 | Takagi et al. |
| 4,280,500 A | 7/1981 | Ono |
| 4,304,010 A | 12/1981 | Mano |
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |

(Continued)

FOREIGN PATENT DOCUMENTS

| | | |
|---|---|---|
| EP | 0 372 088 | 6/1990 |
| EP | 372088 | 6/1990 |

(Continued)

OTHER PUBLICATIONS

Dillon M E, Silicone and Poly (tetrafluoroethylene) Interpenetrating Polymer Networks, 1994 American Chemical Society.

*Primary Examiner* — Nicholas Lucchesi
*Assistant Examiner* — Diva K Chander
(74) *Attorney, Agent, or Firm* — William E. Van Curen

(57) ABSTRACT

The present invention provides a balloon which achieves diameters greater than 6 mm for securement to a catheter. The balloon includes an elastomeric generally hollow pressure expandable body which exhibits essentially radial symmetry and constant length when expanded under an internally applied minimum working pressure from an uninflated state.

41 Claims, 5 Drawing Sheets

(56) References Cited

U.S. PATENT DOCUMENTS

| | | |
|---|---|---|
| 4,573,966 A | 3/1986 | Weikl et al. |
| 4,596,839 A | 6/1986 | Peters |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. |
| 4,713,070 A | 12/1987 | Mano |
| 4,737,219 A | 4/1988 | Taller et al. |
| 4,739,762 A | 4/1988 | Palmaz |
| 4,743,480 A | 5/1988 | Campbell et al. |
| 4,764,560 A | 8/1988 | Mitchell |
| 4,816,339 A | 3/1989 | Tu et al. |
| 4,819,751 A | 4/1989 | Shimada et al. |
| 4,832,688 A | 5/1989 | Sagae et al. |
| 4,896,669 A | 1/1990 | Bhate et al. |
| 4,946,464 A | 8/1990 | Pevsner |
| 4,955,899 A | 9/1990 | Dell Coma et al. |
| 5,041,047 A | 8/1991 | Casale |
| 5,061,276 A | 10/1991 | Tu et al. |
| 5,066,298 A | 11/1991 | Hess |
| 5,071,609 A | 12/1991 | Tu et al. |
| 5,087,244 A | 2/1992 | Wolinsky et al. |
| 5,100,429 A | 3/1992 | Sinofsky et al. |
| 5,108,370 A | 4/1992 | Walinsky |
| 5,112,304 A | 5/1992 | Barlow et al. |
| 5,116,318 A | 5/1992 | Hillstead |
| 5,137,512 A | 8/1992 | Burns et al. |
| 5,147,302 A | 9/1992 | Euteneuer et al. |
| 5,152,782 A | 10/1992 | Kowligi et al. |
| 5,171,297 A | 12/1992 | Barlow et al. |
| 5,192,296 A | 3/1993 | Bhate et al. |
| 5,195,970 A | 3/1993 | Gahara |
| 5,197,978 A | 3/1993 | Hess |
| 5,201,706 A | 4/1993 | Noguchi et al. |
| 5,211,654 A | 5/1993 | Kaltenbach |
| 5,213,576 A | 5/1993 | Abiuso et al. |
| 5,226,880 A | 7/1993 | Martin |
| 5,236,659 A | 8/1993 | Pinchuk et al. |
| 5,254,090 A | 10/1993 | Lombardi et al. |
| 5,256,143 A | 10/1993 | Miller et al. |
| 5,286,254 A | 2/1994 | Shapland et al. |
| 5,290,306 A | 3/1994 | Trotta et al. |
| 5,304,120 A | 4/1994 | Crandell et al. |
| 5,304,214 A | 4/1994 | DeFord et al. |
| 5,304,340 A | 4/1994 | Downey |
| 5,308,356 A | 5/1994 | Blackshear |
| 5,330,429 A | 7/1994 | Noguchi et al. |
| 5,338,299 A | 8/1994 | Barlow |
| 5,342,305 A | 8/1994 | Shonk |
| 5,342,348 A | 8/1994 | Kaplan |
| 5,348,538 A | 9/1994 | Wang et al. |
| 5,358,486 A | 10/1994 | Saab |
| 5,358,516 A | 10/1994 | Myers et al. |
| 5,366,442 A | 11/1994 | Wang et al. |
| 5,366,472 A | 11/1994 | Hillstead |
| 5,370,618 A | 12/1994 | Leonhardt |
| 5,403,340 A | 4/1995 | Wang et al. |
| 5,409,495 A | 4/1995 | Osborn |
| 5,415,636 A | 5/1995 | Forman |
| 5,425,710 A | 6/1995 | Khair et al. |
| 5,429,605 A | 7/1995 | Richling |
| 5,456,661 A | 10/1995 | Narciso |
| 5,458,568 A | 10/1995 | Racchini et al. |
| 5,458,605 A | 10/1995 | Klemm |
| 5,466,252 A | 11/1995 | Soukup et al. |
| 5,470,313 A | 11/1995 | Crocker et al. |
| 5,470,314 A | 11/1995 | Walinsky |
| 5,476,589 A | 12/1995 | Bacino |
| 5,478,320 A | 12/1995 | Trotta |
| 5,478,349 A | 12/1995 | Nicholas |
| 5,484,411 A | 1/1996 | Inderbitzen et al. |
| 5,490,839 A | 2/1996 | Wang et al. |
| 5,496,276 A | 3/1996 | Wang et al. |
| 5,498,238 A | 3/1996 | Shapland et al. |
| 5,499,973 A | 3/1996 | Saab |
| 5,499,980 A | 3/1996 | Euteneuer |
| 5,499,995 A | 3/1996 | Teirstein |
| 5,500,180 A | 3/1996 | Anderson et al. |
| 5,500,181 A | 3/1996 | Wang et al. |
| 5,512,051 A | 4/1996 | Wang et al. |
| 5,519,172 A | 5/1996 | Spencer et al. |
| 5,527,282 A | 6/1996 | Segal |
| 5,529,820 A | 6/1996 | Nomi et al. |
| 5,571,089 A | 11/1996 | Crocker |
| 5,609,605 A | 3/1997 | Marshall et al. |
| 5,613,979 A | 3/1997 | Trotta et al. |
| 5,620,649 A | 4/1997 | Trotta |
| 5,641,373 A | 6/1997 | Shannon et al. |
| 5,645,560 A | 7/1997 | Crocker et al. |
| 5,647,848 A | 7/1997 | Jorgensen |
| 5,716,340 A | 2/1998 | Schweich et al. |
| 5,716,396 A | 2/1998 | Williams, Jr. |
| 5,752,934 A | 5/1998 | Campbell et al. |
| 5,766,201 A | 6/1998 | Ravenscroft et al. |
| 5,797,877 A | 8/1998 | Hamilton et al. |
| 5,807,327 A | 9/1998 | Green et al. |
| 5,843,116 A | 12/1998 | Crocker et al. |
| 5,868,704 A | 2/1999 | Campbell et al. |
| 5,868,708 A | 2/1999 | Hart et al. |
| 5,893,840 A | 4/1999 | Hull et al. |
| 5,908,406 A | 6/1999 | Ostapchenko et al. |
| 5,944,734 A | 8/1999 | Hermann et al. |
| 5,951,941 A | 9/1999 | Wang et al. |
| 5,954,745 A | 9/1999 | Gertler et al. |
| 5,972,441 A | 10/1999 | Campbell et al. |
| 6,010,480 A | 1/2000 | Abele et al. |
| 6,013,092 A | 1/2000 | Dehdashtian |
| 6,027,779 A | 2/2000 | Campbell et al. |
| 6,048,356 A | 4/2000 | Ravenscroft et al. |
| 6,120,477 A | 9/2000 | Campbell et al. |
| 6,132,824 A | 10/2000 | Hamlin |
| 6,234,995 B1 | 5/2001 | Peacock, III |
| 6,287,290 B1 | 9/2001 | Perkins et al. |
| 6,287,314 B1 | 9/2001 | Lee et al. |
| 6,319,249 B1 | 11/2001 | Tollner |
| 6,319,259 B1 | 11/2001 | Lee et al. |
| 6,319,529 B1 | 11/2001 | Thompson |
| 6,336,937 B1 | 1/2002 | Vonesh et al. |
| 6,375,637 B1 | 4/2002 | Campbell et al. |
| 6,428,506 B1 | 8/2002 | Simhambhatla et al. |
| 6,482,348 B1 | 11/2002 | Wang et al. |
| 6,488,688 B2 | 12/2002 | Lim et al. |
| 6,572,813 B1 | 6/2003 | Zhang et al. |
| 6,602,224 B1 | 8/2003 | Simhambhatla |
| 6,663,646 B1 | 12/2003 | Shah |
| 6,746,425 B1 | 6/2004 | Beckham |
| 6,756,094 B1 | 6/2004 | Wang et al. |
| 6,887,227 B1 | 5/2005 | Barbut |
| 6,890,395 B2 | 5/2005 | Simhambhatla |
| 6,905,743 B1 | 6/2005 | Chen et al. |
| 6,923,827 B2 | 8/2005 | Campbell et al. |
| 6,939,593 B2 | 9/2005 | Wang |
| 6,977,103 B2 * | 12/2005 | Chen et al. .................. 428/35.7 |
| 7,052,507 B2 | 5/2006 | Wakuda et al. |
| 7,195,638 B1 | 3/2007 | Sridharan |
| 7,279,208 B1 | 10/2007 | Goffena et al. |
| 7,306,729 B2 | 12/2007 | Bacino et al. |
| 7,625,337 B2 | 12/2009 | Campbell et al. |
| 7,785,290 B2 * | 8/2010 | Alpini et al. ............. 604/103.06 |
| 2001/0008970 A1 | 7/2001 | Ravenscroft et al. |
| 2002/0087165 A1 | 7/2002 | Lee et al. |
| 2002/0163104 A1 | 11/2002 | Motsenbocker |
| 2003/0074016 A1 | 4/2003 | Campbell et al. |
| 2003/0083687 A1 | 5/2003 | Paliazza |
| 2003/0088209 A1 | 5/2003 | Chiu et al. |
| 2003/0130716 A1 | 7/2003 | Weber |
| 2003/0211258 A1 * | 11/2003 | Sridharan et al. ............ 428/35.2 |
| 2004/0015183 A1 * | 1/2004 | Lim et al. ...................... 606/194 |
| 2004/0082965 A1 * | 4/2004 | Beckham ...................... 606/192 |
| 2004/0191442 A1 | 9/2004 | Lim |
| 2004/0199202 A1 | 10/2004 | Dubrul et al. |

(56) References Cited

U.S. PATENT DOCUMENTS

| | | |
|---|---|---|
| 2004/0254625 A1 | 12/2004 | Stephens et al. |
| 2005/0015048 A1 | 1/2005 | Chiu et al. |
| 2005/0038503 A1 | 2/2005 | Greenhalgh et al. |
| 2005/0267409 A1 | 12/2005 | Shkolnik |
| 2005/0273152 A1 | 12/2005 | Campbell et al. |
| 2006/0085024 A1 | 4/2006 | Pepper et al. |
| 2006/0136032 A1* | 6/2006 | Legarda et al. ............... 623/1.11 |
| 2006/0161102 A1 | 7/2006 | Newcomb et al. |
| 2006/0271091 A1* | 11/2006 | Campbell et al. ............. 606/192 |
| 2007/0055301 A1 | 3/2007 | Campbell et al. |
| 2007/0061000 A1 | 3/2007 | Campbell et al. |
| 2007/0219489 A1 | 9/2007 | Johnson et al. |
| 2008/0125711 A1 | 5/2008 | Alpini et al. |
| 2008/0140173 A1 | 6/2008 | Eskaros et al. |
| 2008/0255507 A1 | 10/2008 | Mushtaha |
| 2008/0257155 A1 | 10/2008 | Bacino et al. |
| 2008/0312730 A1 | 12/2008 | Campbell et al. |
| 2009/0032470 A1 | 2/2009 | Bacino et al. |
| 2009/0053103 A1 | 2/2009 | Mortimer et al. |
| 2009/0283206 A1 | 11/2009 | Eskaros et al. |
| 2010/0049123 A1 | 2/2010 | Alpini et al. |
| 2010/0262178 A1 | 10/2010 | Alpini et al. |

FOREIGN PATENT DOCUMENTS

| | | |
|---|---|---|
| EP | 0 540 858 | 5/1993 |
| EP | 0 628586 | 12/1994 |
| EP | 737488 | 10/1996 |
| EP | 769307 | 4/1997 |
| EP | 0 829 269 | 3/1998 |
| GB | 1566674 | 5/1980 |
| NL | 1008178 | 8/1999 |
| WO | 90/14054 | 11/1990 |
| WO | 94/02185 | 2/1994 |
| WO | 95/05555 | 2/1995 |
| WO | 95/09667 | 4/1995 |
| WO | 95/17920 | 7/1995 |
| WO | 96/14895 | 5/1996 |
| WO | 96/40350 | 12/1996 |
| WO | 97/02791 | 1/1997 |
| WO | 97/40877 | 11/1997 |
| WO | 02/68011 | 9/2002 |
| WO | 03/000307 | 1/2003 |
| WO | 2008/021002 | 2/2008 |
| WO | 2008/021003 | 2/2008 |
| WO | 2008/021006 | 2/2008 |
| WO | 2008/021013 | 2/2008 |

* cited by examiner

NON-SHORTENING HIGH ANGLE WRAPPED BALLOONS

CROSS REFERENCE TO RELATED APPLICATIONS

This application is a continuation of application Ser. No. 11/501,190, filed Aug. 7, 2006 now U.S. Pat. No. 7,785,290.

BACKGROUND OF THE INVENTION

The present invention relates to balloon catheters and, more particularly, to a non-shortening wrapped balloon configured to expand to a predetermined diameter upon application of a predetermined pressure thereto.

Balloon catheters are well known in the art. Such catheters are employed in a variety of medical procedures, including dilation of narrowed blood vessels, placement of stents and other implants, temporary occlusion of blood vessels, and other vascular uses.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter.

Procedures such as these are generally considered minimally invasive, and are often performed in a manner which minimizes disruption to the patient's body. As a result, catheters are often inserted from a location remote from the region to be treated. For example, during angioplasty procedures involving coronary vessels, the balloon catheter is typically inserted into the femoral artery in the groin region of the patient, and then advanced through such vessel into the coronary region of the patient. These catheters typically include some type of radiopaque marker to allow the physician performing the procedure to monitor the progress of the catheter through the body. As a characteristic of wrapped balloons, it is also common to have the length of the wrapped balloon change during inflation causing placement problems during procedures. Additionally, catheters have been unable to deliver balloons with large diameters expansion capability due to the need for a low profile and sustained high pressures.

There are two main forms of balloon catheter devices. Non-compliant catheters employ a balloon made of relatively strong but generally inelastic material (e.g., polyester) folded into a compact, small diameter cross section. These relatively stiff catheters are used to compact hard deposits in vessels. Due to the need for strength and stiffness, these devices are rated to employ high inflation pressures, usually up to about 8 to 18 atmospheres. They tend to be self-limiting as to diameter in that they will normally distend up to the rated diameter and not distend appreciably beyond this diameter until rupture due to over-pressurization. While the inelastic material of the balloon is generally effective in compacting deposits, it tends to collapse unevenly upon deflation, leaving a flattened, wrinkled bag, substantially larger in cross section than the balloon was when it was originally installed. This enlarged, wrinkled, relatively stiff bag may be difficult to remove, especially from small vessels.

By contrast, compliant catheters employ a soft, very elastic material (e.g., natural rubber latex) as the balloon. These catheters are employed to displace soft deposits, such as thrombus, where a soft and tacky material such as latex provides an effective extraction means, and also can be used as an occlusion balloon, though operate at low pressures. Latex and other highly elastic materials generally will expand continuously upon increased internal pressure until the material bursts. As a result, these catheters are generally rated by volume (e.g., 0.3 cc) in order to properly distend to a desired size. Although relatively weak, these catheters do have the advantage that they tend to readily return to their initial size and dimensions following inflation and subsequent deflation.

Some catheter balloons constructed of both elastomeric and non-elastomeric materials have been described previously. U.S. Pat. No. 4,706,670 describes a balloon dilatation catheter constructed of a shaft made of an elastomeric tube and reinforced with longitudinally inelastic filaments. This device incorporates a movable portion of the shaft to enable the offset of the reduction in length of the balloon portion as the balloon is inflated. One improved balloon is disclosed in U.S. Pat. No. 4,706,670 teaching reinforcing filaments in a balloon portion at an angle which is less than 54.73 degrees relative to the axis of the balloon. As the length of the balloon portion decreases, the length of the movable portion of the outer tubing increases and by proper selection of internal diameters and lengths of the two portions, the shortening of the balloon is offset.

U.S. Pat. No. 5,647,848 teaches a structure formed of helically extending fibers, including bundles of continuous monofilaments, aramide, polyethylene, steel, polyester, glass, carbon, and ceramics. The fibers are positioned in an elastomer such that the fibers lie at an angle which is less than a neutral angle of 54.73 degrees relative to the axis of the balloon when the balloon is unpressurized. With the utilization of rigid fibers the balloon will be non-compliant in its fully inflated state. The difference in rigidity although desirable with respect to independent movement of the components of the balloon can introduce unwanted torsional moments into the elastomeric balloon depending upon the construction of the balloon and fibers.

Accordingly, there is a need in the art for a soft, high pressure, large diameter, high expansion ratio (greater than 400 percent) balloon which does not lengthen or shorten upon inflation and has a predefined maximum expanded diameter. This maximum expanded diameter should remain constant even as the pressure of the balloon is increased. Moreover, this maximum expanded diameter should remain essentially constant upon repeated inflation and deflation of the balloon. The present invention fulfills this need.

SUMMARY OF THE INVENTION

The present invention provides a non-shortening, wrapped catheter balloon. The balloon comprises a wrapped membrane. The wrapped membrane provides an outer limit constraint for expansion of the balloon body to a predetermined maximum diameter at a minimum working pressure. If desired, the wrapped membrane may also provide a seal for the balloon.

The balloon of the present invention is able to realize a ratio of final-to-initial overall catheter diameter (inflated balloon to leg outer diameter) of greater than 400 percent without foreshortening or lengthening.

DETAILED DESCRIPTION OF THE INVENTION

The present invention provides a soft, high pressure, large diameter (considered to be balloons of greater than 10 mm and for the purposes of this invention to balloons over 18 mm inflated), high expansion ratio balloon which does not lengthen, for securement to a catheter. The balloon comprises a plurality of wrapped layers formed into a generally hollow pressure expandable body which exhibits essentially radial symmetry when expanded under an internally applied minimum working pressure from an uninflated state. The wrapping provides an outer limit constraint for expansion of the balloon body to a predetermined maximum diameter at a minimum working pressure.

A balanced force balloon of the present invention is a balloon possessing a combination of passes to create the strength to balance the radial force exerted by inflation pressures on the balloon vessel with respect to the longitudinal forces exerted by inflation so that the balloon inflates to its desired diameter without any longitudinal movement.

For a helically wrapped cylindrical pressure vessel, the balanced force would lie along the force resultant angle of 54.7 degrees between the radial force vector and the longitudinal force vector. In this invention the balance force is also created by wrapping in longitudinal and axial components of the balance force angle.

Figure 1:
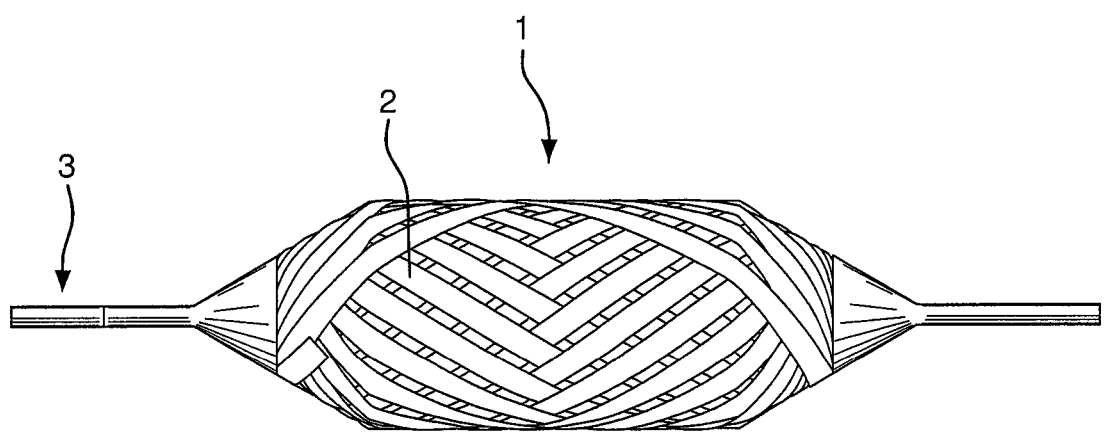
FIG. 1 shows a schematic of a non-distensible balloon.

As shown in FIG. 1, the catheter balloon of this invention is unique in that it provides the first soft, high pressure, high expansion ratio, non-shortening, non-compliant balloon 1. This catheter balloon is capable of achieving large (greater than 10 mm) inflated diameters at high pressures greater than 6 atm, and even greater than 10 atm, while still maintaining competitive crossing profiles. The catheter balloon comprises a longitudinal axis and further comprises at least two passes 2 of a composite wrap which forms the balloon structure. The balloon is mounted on a hypotube 3 or may alternatively be mounted on a catheter shaft.

A longitudinal pass is comprised of one or more layers of material which are laid at similar angles in relation to the longitudinal axis of the balloon. A longitudinal pass comprises a distinctive layer or series of layers of material which are wound or wrapped to form a region or area distinct from surrounding or adjoining parts. It is important to note that a pass may span the entire length of the balloon or in certain instances, such as non-distending or non-inflating regions, the pass may span only a partial length of the balloon.

A layer is considered to be one strand, strip or thickness of balloon material which may be wrapped, folded, laid or weaved over, around, beside or under another strand, strip or thickness of balloon material.

While it is clear that a longitudinal pass may span the entire length of the balloon at a single wrap angle, a longitudinal pass may also comprise a wrapping event in which the wrapping angles may be changed during the continuous longitudinal wrapping so that in this type of wrapping pattern a single pass may include two or more wrap angles.

In one embodiment, at least one base layer is provided around the longitudinal axis in an essentially longitudinal direction. At least one radial layer is wrapped around the longitudinal axis in an essentially circumferential direction with respect to the longitudinal axis. At least one helical layer is oriented helically in the direction of the maximum hoop stress to create a high pressure balloon. The three types of layers operate in conjunction to provide a balloon with balanced forces upon inflation. A sufficient number of layers will provide a targeted high-pressure balloon (see FIGS. 1, 5, 6, 7, 8, and 9 for all three layers).

Figure 2:
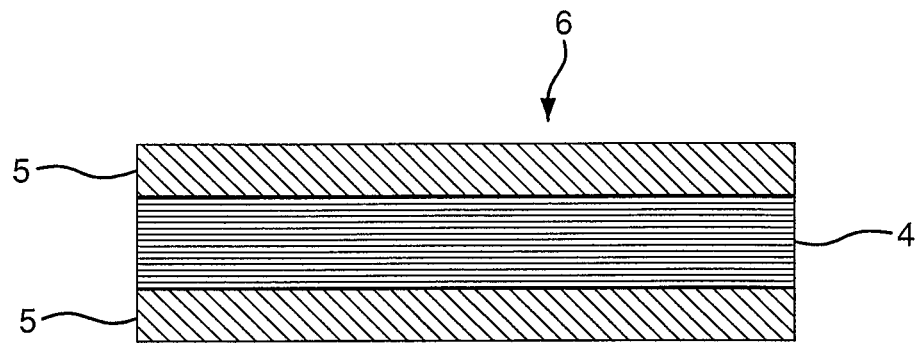
FIG. 2 shows a cross-section of a composite film with two polymer coating layers.
Figure 3:
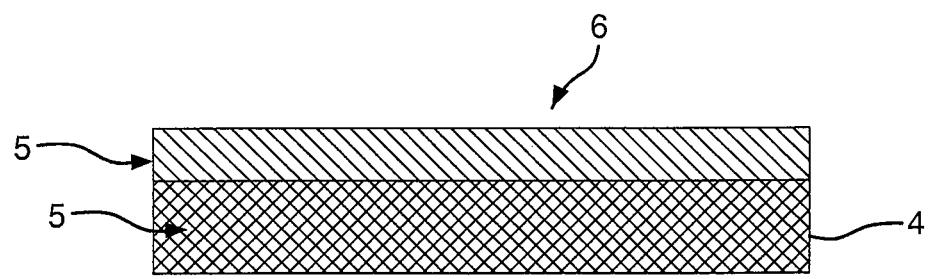
FIG. 3 shows a cross-section of a composite film with one polymer coating layer.
Figure 4:
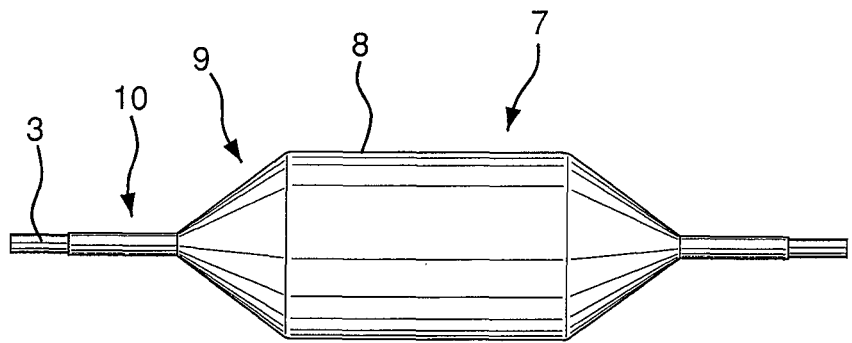
FIG. 4 shows a mandrel used to wrap and shape the balloon.

As shown in FIGS. 2 and 3, the composite film 6 is formed of a porous membrane 4, for example, such a membrane may be comprised of a polytetrafluoroethylene (PTFE) or an expanded polytetrafluoroethylene (ePTFE). The balloon of the present invention comprises multiple passes of material wrapped with force balance at full size diameter. Each pass is wrapped at different angles. In a preferred embodiment, at least three passes are used. The membrane 4 is coated with a polymer coating 5 on at least one side and imbibed throughout the membrane to form a strong thin composite film 6. The composite film may be cut or slit into thinner sections to make a composite film wrap. The total polymer weight in an application may vary depending on the desired application and with regard to ePTFE, is typically between approximately 40 percent to 60 percent of the total final composite film weight. The at least two wrapping layers are wrapped at the final balloon diameter around a mandrel and then deflated to ensure an accurate final diameter upon re-inflation. The mandrel 7, as shown in FIG. 4, comprises a distal and proximal end each with a working length, shoulder and leg. The working length 8 is the part of the mandrel which extends the between the proximal shoulder and the distal shoulder of the mandrel body. The shoulder 9 may be tapered in desired embodiments. The shoulder 9 on the distal end of the mandrel is located between the end of the working length 8 and the leg 10 on the distal end of the mandrel. Similarly, the shoulder on the proximal end of the mandrel 7 is located between the end of the working length and the leg on the proximal end of the mandrel. Due to the orientation of the wrapping layers to each other, and wrapping at the final diameter, transverse strain of the wrapped material caused by inflation is prevented, allowing expansion ratios of greater than 400 percent. Transverse strain is an increase in material width as a low angle wrapped balloon rotates to the balanced force angle of 54.7 degrees during inflation. This width growth can be described by the following relationship (Width$_F$=Width$_I$×(cos θ$_F$/cos θ$_I$)$^2$× (tan θ$_F$/tan θ$_I$) where F is Final and I is initial. This strain can exceed 500 percent in some balloons depending on the deflated to inflated diameter ratio. In a low angle wrapped balloon, anisotropic materials must be used.

In one aspect, a soft, high pressure, large diameter, high expansion ratio balloon comprises a balloon having a longitudinal axis and at least two passes of wrapped film at a balanced force angle of essentially 54 degrees such that a catheter balloon is formed which achieves an expansion ratio of equal or greater than 400 percent upon inflation of the catheter balloon. The expansion ratio is measured by dividing the inflated diameter of the balloon, measured between the shoulders by the leg diameter. This result is then multiplied by 100 to obtain a percent expansion ratio.

In another aspect, a non-shortening catheter balloon of the present invention is able to withstand increased burst pressures due to the wrapping of the film or other suitable material in an essentially longitudinal direction and then the wrapping of a second film or other suitable material in an essentially helical direction around a mandrel. The mandrel has an outer dimension which is equal to the desired final inflated internal diameter of the catheter balloon. The wrapping of the mandrel ceases when the required thickness for the desired strength is achieved. This is determined by the following equations:

The required wrap thickness to hold diameter in place is calculated as:

$t_f = PR/2S_f \text{SIN}^2 A$ (for 54.7 degree wrap)

The longitudinal force required to hold balloon in place is calculated as:

$$t_f = PR/S_f \cos^2 A$$

where:
A=angle
$S_f$=allowable stress of film in P.S.I.
$t_f$=thickness of film in inches
P=pressure (inflation) P.S.I.
R=radius of inflated balloon in inches The balloon structure diameter is then minimized by removing the mandrel or decreasing the outer diameter of the mandrel to create a soft, high pressure, large diameter, high expansion ratio (greater than 400 percent) balloon.

The non-compliant balloon is constructed by wrapping a composite film around the mandrel. In one preferred embodiment an ePTFE membrane is used to make the composite film. The ePTFE membrane is made in accordance with the teaching in U.S. Pat. No. 5,476,589, incorporated herein by reference. The ePTFE membrane is longitudinally expanded to a ratio of 55 to 1 and transversely expanded approximately 2.25 to 1, to produce a thin strong membrane with a mass of between 2 to 8 g/m² and a thickness of 2.5 to 7.5 micrometers. A 0.5 percent to 8 percent by weight solution of polyurethane to tetrahydrofuran (THF) is coated onto the ePTFE membrane to produce a composite film with polyurethane on at least one side and throughout the ePTFE membrane. The total polymer weight in an application may vary depending on the desired application, and is typically between approximately 40 percent to 60 percent of the total final composite film weight. The composite film for the radial passes may vary in width and may be equal to or less than the balloon working length. The composite film width of the longitudinal and helical wrap passes are preferably about 0.10 of the final inflated diameter of the balloon. However, while this width is preferable, other widths of film may be used to obtain the desired final thickness of the helically and longitudinally oriented wrap passes. The composite film may vary in width. While the longitudinal and transverse expansion ratios stated above are preferred, other suitable expansion ratios may be used as would be known to one of skill in the art.

The present invention eliminates the problem of transverse strain associated with other wrapped balloons. Some balloons wrapped at less than their final diameter encountered transverse strain on the material upon expansion. The present invention is wrapped at its final diameter to alleviate associated transverse strain. Additionally, the composite film of the present invention may be anisotropic or isotropic. In a preferred embodiment, the film is anisotropic.

As shown in FIGS. 5-9, different wrap patterns may be used to wrap the mandrel, and to provide balanced forces upon inflation. The wrap angle is adjusted to allow for different wrap configurations. Adequate tension is employed to keep the composite film taut. A variety of wrapping patterns applied in any order may be used to make the non-compliant balloons of the present invention. In one embodiment, as set forth in Examples 2-10, a soft, high pressure, large diameter, high expansion ratio (greater than 400 percent) balloon designed for large diameter, high burst pressure is achieved, comprising at least one radial layer; at least one base layer; and at least one helical layer. Other configurations may be designed depending upon the desired attributes of the finished balloon.

Figure 5:
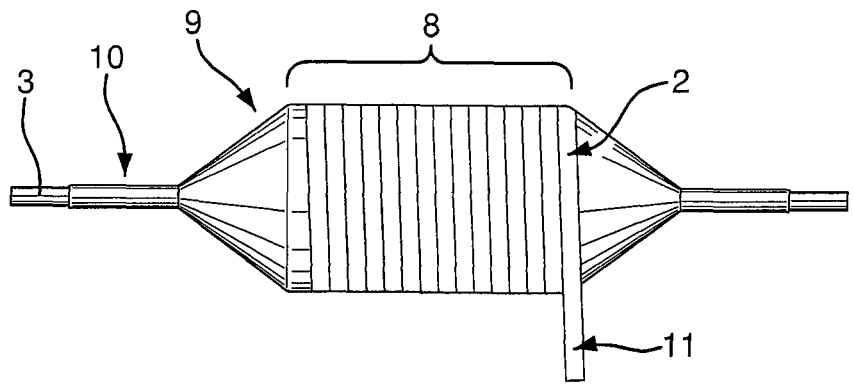
FIG. 5 shows a wrap schematic of a radial layer.

As shown in FIG. 5, the radial pass is comprised of wrapped layers wound around the working length 8 of the mandrel from one shoulder 9 to the next shoulder in a conventional shaped balloon. Herein, a conventional shaped balloon is one with its fullest diameter in the middle of the balloon and having two legs 10 or small diameters in contact with a hypotube 3 or catheter shaft. The diameters of the legs 10 do not need to be equal. Other wrap configurations may be employed for balloons with non-conventional shaped mandrels.

Figure 6:
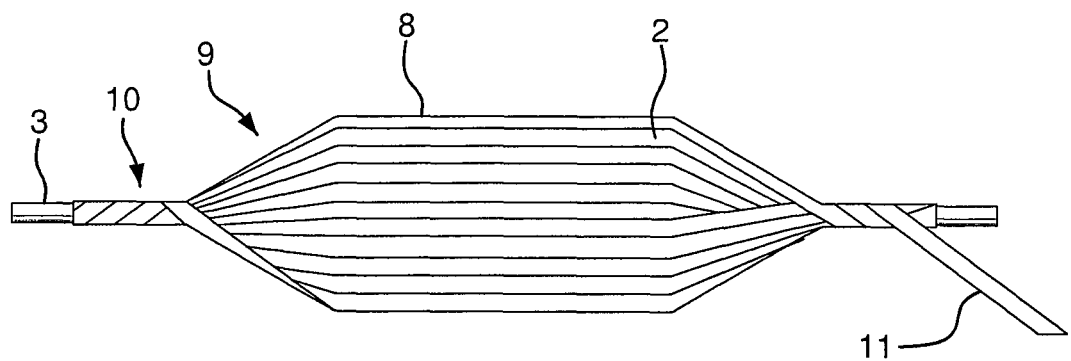
FIG. 6 shows a wrap schematic of a base layer.

As shown in FIG. 6, a base pass, may be constructed by positioning the composite film wrap 11 and wrapping it around the mandrel and over the radial layer. The base pass is comprised of wrapped layers which may be used to wrap the legs 10 of the balloon for attachment to a hypotube 3 or catheter shaft. In the base layer wrap, both legs should be wrapped at an angle (measured from the mandrel axis) equal or greater than the angle of the shoulder wrap layers. The shoulders 9 and working length 8 of the balloon receive at least one pass of base layer wrap during this wrap, while the legs receive a plurality of base wrap layers.

Figure 7:
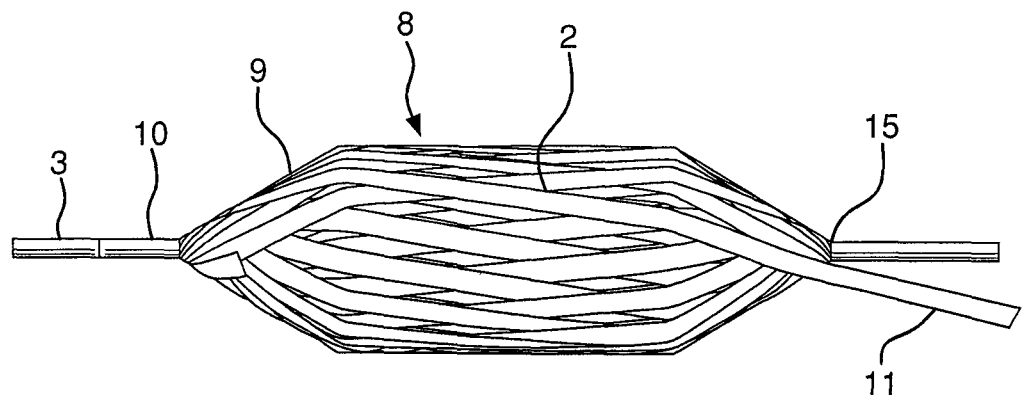
FIG. 7 shows a wrap schematic of a first helical layer.
Figure 8:
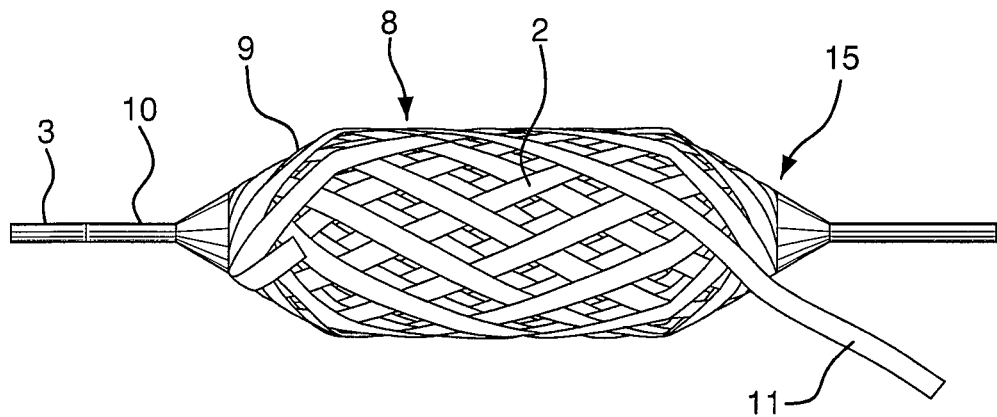
FIG. 8 shows a wrap schematic of a second helical layer.
Figure 9:
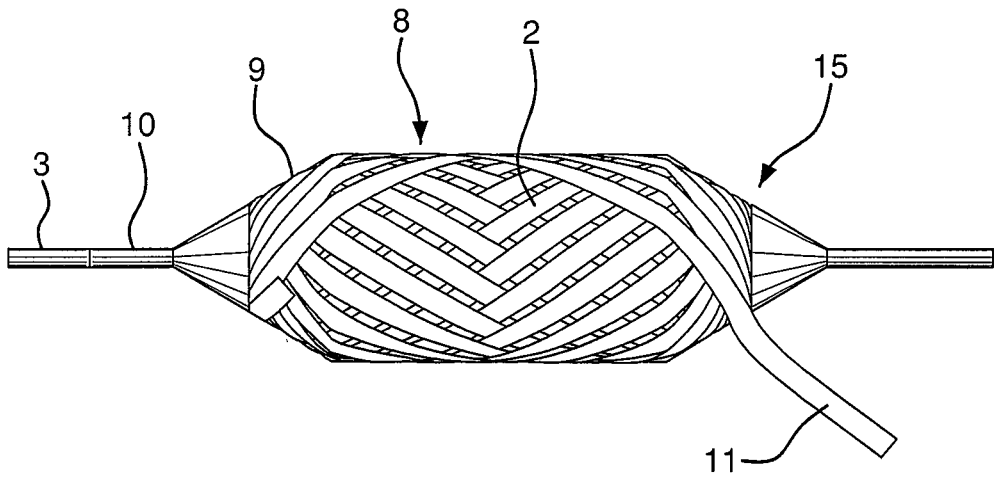
FIG. 9 shows a wrap schematic of a third helical layer.

As shown in FIGS. 7-9, the helical layer is formed by wrapping the balloon working length and shoulders at a desired angle. If wrapped along the geodesic (non-slip) path, the desired angle will result in a wrap that extends down the axial length of the balloon shoulder 9, terminates at a pole opening 15, then extends in the opposite direction over the balloon working length 8 and down the opposite shoulder 9 to the opposite pole opening. If there is friction between the film and mandrel or previous layers, wrapping on the geodesic path is not necessary. The friction may be provided by an affinity of the film to itself or the mandrel. In addition, agents, such as adhesives, may be employed to provide friction. At the pole openings, the composite film loops around the mandrel composite to change wrap direction. This looping of the film results in a disproportionate thickness of the film at the pole opening as compared to the film thickness over the balloon working length.

To mitigate excess film buildup, subsequent helical passes may be wrapped at different angles to vary the pole opening, over the length of the balloon shoulder, as shown in FIGS. 7-9. This results in a balloon shoulder with more consistent film thickness. It is not necessary to employ any specific order of helical wrap patterns. Similarly, it is not necessary for the radial, base, or helical passes (FIGS. 5-9) to be wrapped in any specific order in relation to each other.

The number of passes, types of passes, and wrap patterns which are employed to wrap the mandrel and form a non-distensible catheter balloon 2 can vary depending upon the desired profile and/or application. A tubular catheter shaft having a longitudinal axis with a proximal end and a distal end may be used to mount the balloon for delivery. The catheter shaft comprises at least one inflation lumen extending from an inflation port and extends distally to a location proximally spaced from the distal end. The inflatable balloon can be affixed near the distal end of the catheter shaft. The balloon has an interior chamber in fluid communication with the inflation lumen. The interior chamber is formed by minimization of the mandrel upon completion of wrapping the composite film wrap 11 to form a balloon structure. The mandrel in the formed balloon structure may be minimized by deflating the mandrel; by dissolving or melting the mandrel; by deflating and removing the mandrel; or by another means known to one in the art. The mandrel may further comprise an inflatable bladder. The bladder may be comprised of a single piece; multiple pieces or a material or film wrapped in a continuous manner to form a bladder. When present as an inflatable bladder, the mandrel may remain as part of finished device.

In an additional embodiment, a catheter balloon is provided. The catheter balloon may be comprised of any suitable materials, but in a preferred construct the soft, high pressure, large diameter, high expansion ratio (greater than 400 percent) balloon comprises a porous membrane, such as ePTFE or other suitable porous materials. The polymer coating 5 may be comprised of any suitable materials known to one in the art including but not limited to polyurethanes and fluorinated polymers. The balloon has a pre-inflated shape with a substantially circular cross-section when opposing ends of the balloon are affixed to the catheter shaft. The balloon has a balloon length measured between its opposing ends, wherein the length varies less than ten percent between when the balloon is in a deflated state as compared to the length of the balloon inflated to a predetermined burst pressure. In preferred applications, the balloon does not change length by more than 5 percent upon inflation to a rated burst pressure. In further preferred applications, the balloon does not change length by more than 2 percent upon inflation to a rated burst pressure. An expandable stent or other medical device may be disposed about the balloon or mounted onto the balloon for delivery into a patient's body. Inflation of the balloon occurs in an essentially radially symmetric manner. Accordingly expansion of a stent mounted thereon is also essentially radially symmetric. Upon deflation of the balloon it is substantially returned to its preinflated shape. The present invention solves the clinical issues of accurate placement of a balloon or stent due to foreshortening of traditional wrapped balloons. The present invention also prevents undue trauma on vessel endothelial layers and possibility of plaque fragmentation caused by inflation movement of asymmetric inflating balloons.

The mold for a balloon mandrel may be constructed with a desired internal balloon shape. The size of the mandrel may vary to achieve diameters greater than 10 mm in diameter. The shoulders of the balloon shaped mold may be blunt or tapered. The taper is measured with respect to the mandrel axis to a leg of a given diameter. The leg may be of any desired length and diameter. In a preferred balloon mold, the leg is stepped down to create a shutoff with respect to a contacting hypotube. It is desired that a fill hole large enough to accept a syringe barrel tip is incorporated at a point on the balloon working length, for instance on the mold separation line. Appropriate vents may also be added at the terminus of each leg. The resulting balloon mandrel may be wrapped by a wrapping machine (mandrel rotation, x-axis, and y-axis). The balloon mandrel can be mounted by gripping the ends of the hypotube that extends through the balloon shaped mandrel. The wrapping film can be positioned so that the material film can change wrapping directions as desired on the base layer and other employed layers as described above Further, the catheter balloon made in accordance with the present invention is able to achieve an inflation ratio of equal to or greater than 400 percent upon inflation of the catheter balloon without experiencing any foreshortening or lengthening of the balloon from its preinflated length. The catheter balloon may comprise sections wrapped at differing angles to allow for semi-compliant and non-compliant sections. The catheter balloon may be wrapped into various desired shapes including a conventional balloon shape, a non-tubular shape, a sphere, a barbell formation, or other desired shapes.

The non-shortening catheter balloon of the present invention exhibits increased burst pressures over traditional balloons and may be formed by wrapping a film or other suitable material around a mandrel having a outer dimension of the desired final inflated internal diameter of the catheter balloon. The wrap forms a plurality of oriented passes with respect to the longitudinal axis. The film passes are oriented to achieve a balanced force for the balloon modeled as a pressure vessel upon inflation. The mandrel is continuously wrapped until a final desired strength of the catheter balloon is achieved with the plurality of film layers to form a balloon structure. When the wrap configuration pattern or recipe is completed and all wrap layers have been applied, the wrapped mandrel may be heated at above ambient temperatures to set the wrap layers in place. The temperature chosen to set the layers is dependent upon the materials used in construction of the formed balloon structure, but should be high enough and long enough to adhere the layers together. The mandrel should be allowed to cool prior to removal or minimization of the mandrel. The balloon structure diameter is then minimized by removing the mandrel or decreasing the outer diameter of the mandrel to create a non-shortening catheter balloon with increased burst pressures. The minimization of the balloon structure is achieved by deflating the mandrel; dissolving or melting the mandrel; deflating and removing the mandrel or in any other suitable manner. The mandrel may comprise an inflatable bladder. The mandrel may remain as part of finished device. The bladder may be formed of a single piece unit, multiple pieces, or may be wrapped in a continuous manner.

The composite film of the present invention comprises a porous reinforcing layer and a continuous polymer layer. The porous reinforcing polymer layer is a thin, strong porous membrane that may be made in sheet form. The porous reinforcing polymer can be selected from a group of polymers including, but not limited to, olefin, PEEK, polyamide, polyurethane, polyester, polyethylene, and polytetrafluoroethylene. In preferred embodiments, the porous reinforcing polymer is expanded polytetrafluoroethylene (ePTFE) made in accordance with the general teachings of U.S. Pat. No. 5,476,589 or U.S. patent application Ser. No. 11/334,243 incorporated herein by reference. In this embodiment, the ePTFE membrane is anisotropic such that it is highly oriented in the one direction. An ePTFE membrane with a matrix tensile value in one direction of greater than 690 megapascals is preferred, and greater than 960 megapascals is even more preferred, and greater than 1,200 megapascals is most preferred. The exceptionally high matrix tensile value of ePTFE membrane allows the composite material to withstand very high hoop stress in the inflated balloon configuration. In addition, the high matrix tensile value of the ePTFE membrane makes it possible for very thin layers to be used which reduces the deflated balloon profile. A small profile is necessary for the balloon to be able to be positioned in small arteries or veins or orifices. In order for balloons to be positioned in some areas of the body, the balloon catheter must be able to move through a small bend radius, and a thinner walled tube is typically much more supple and capable of bending in this manner without creasing or causing damage to the wall of the vessel.

In another embodiment, the ePTFE membrane is relatively mechanically homogeneous. The mechanically balanced ePTFE membrane can increase the maximum hoop stress that the composite film made therefrom can withstand.

The continuous polymer layer of the present invention is coated onto at least one side of the porous reinforcing polymer. The continuous polymer layer is preferably an elastomer, such as, but not limited to, aromatic and aliphatic polyurethanes including copolymers, styrene block copolymers, silicones, preferably thermoplastic silicones, fluorosilicones, fluoroelastomers, THV and latex. In one embodiment of the present invention, the continuous polymer layer is coated onto only one side of the porous reinforcing polymer. However, continuous polymer layer may be coated onto both sides of the porous reinforcing polymer. In a preferred embodiment, the continuous polymer layer is imbibed into the porous reinforcing polymer and the imbibed polymer fills the pores of the porous reinforcing polymer.

The continuous polymer layer can be applied to the porous reinforcing polymer through any number of conventional methods including, but not limited to, lamination, transfer roll coating, wire-wound bar coating, reverse roll coating, and solution coating or solution imbibing. In a preferred embodiment, the continuous polymer layer is solution imbibed into the porous reinforcing polymer. In this embodiment, the continuous polymer layer is dissolved in a suitable solvent and coated onto and throughout the porous reinforcing polymer using a wire-wound rod process. The coated porous reinforcing polymer is then passed through a solvent oven and the solvent is removed leaving a continuous polymer layer coated onto and throughout the porous reinforcing polymer. In some cases, such as when silicone is used as the continuous polymer layer, the coated porous reinforcing polymer may not require the removal of solvent. In another embodiment, the continuous polymer layer is coated onto at least one side of the porous reinforcing polymer and maintained in a "green" state where it can be subsequently cured. For example, an ultraviolet light (UV) curable urethane may be used as the continuous polymer layer and coated onto the porous reinforcing polymer. The composite film comprising the porous reinforcing polymer and the UV curable urethane continuous polymer layer can then be wrapped to form at least one layer of the balloon and subsequently exposed to UV light and cured. A pass is considered to be a number of layers applied in a wrapping event. A layer, by contrast, is considered to be a single thickness of composite film wrapped around the balloon.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1

Mandrel Preparation

Aluminum clamshell molds were machined with an internal balloon shape of 25 mm in diameter and 40 mm working length. The shoulders of the balloon shaped mold were tapered at an angle of 30 degrees, with respect to the mandrel axis, to a leg diameter of 2.3 mm. The axial length of the shoulder was 22.7 mm. The leg was 10 mm long. The leg stepped down to create a shutoff with a 0.914 mm diameter hypotube. A fill hole large enough to accept a syringe barrel tip was machined in the middle of the balloon working length, at the mold separation line. Appropriate vents were machined at the terminus of each leg. Before use, the mold was cleaned and lightly coated with a Lecithin based lubricant. A 0.914 mm diameter×152 mm length hypotube, PN B-HTX-20HW (Small Parts, Miami, Fla.), was lightly sandblasted to roughen the surface, and placed in the mold.

A slurry of water and Aquapour™ (Advanced Ceramics Research, Tucson, Ariz.) ceramic powder was mixed, at a ratio of 55 percent by weight Aquapour™ powder to 45 percent by weight water, and injected into the mold with a syringe. The mold was allowed to sit for one hour before the mandrel was removed from the mold and cured in an oven at 135° C. for 1 hour.

The balloon mandrel was loaded onto a 3-axis wrapping machine (mandrel rotation, x-axis, and y-axis). The balloon mandrel was mounted by gripping the ends of the hypotube that extended through the ceramic balloon shape. A small piece of double stick tape was wound onto the hypotube adjacent to the ceramic balloon mandrel leg. The tape provided friction for positioning the film and for changing material directions on the Base Layer.

Example 2

Composite Film

The non-distensible balloon was constructed by wrapping a composite film around the mandrel. The composite film was made by using a wire-wound rod coating process whereby a solution of Tecothane TT-1085A polyurethane and tetrahydrofuran (THF) was coated onto an ePTFE membrane. The ePTFE membrane used to make the composite film was made in accordance with the teaching in U.S. Pat. No. 5,476,589 to Bacino, incorporated herein by reference. Specifically, the ePTFE membrane was longitudinally expanded to a ratio of 55 to 1 and transversely expanded approximately 2.25 to 1, to produce a thin strong membrane with a mass of approximately 3.5 g/m$^2$ and a thickness of approximately 6.5 micrometers. A 3 percent to 8 percent by weight solution of Tecothane TT-1085A polyurethane in THF was coated onto the ePTFE membrane to produce a composite film with approximately equal amounts of Tecothane TT-1085A polyurethane on either side and throughout the ePTFE membrane and a total polymer weight application of approximately 40 percent to 60 percent of the total final composite film weight.

Example 3

Balloon Construction

The composite film was slit to 2.5 mm wide, and stack wound onto a 76 mm diameter core that was placed onto a payoff cart. The payoff cart angle could be adjusted to allow for different wrap configurations. Adequate tension was employed to keep the composite film taut. CADWIND NG 2005 (High End) software (Material Co., Brussels, Belgium) was utilized to develop the film wrap patterns. A variety of wrapping patterns could be used to make the non-distensible balloons of the present invention. The following wrapping layer arrangement recipe is for a 15 atmosphere burst pressure design strength non-distensible balloon:

---

Radial
Base
Radial
Helical 1
Radial
Helical 2
Radial
Helical 3
Radial
Radial
Helical 1
Radial
Radial
Helical 2
Radial

| |
|---|
| Radial |
| Helical 3 |
| Radial |
| Radial |

Example 4

Radial Layer

For the radial layer, the film was positioned by manually wrapping it around the balloon mandrel and onto itself. The film adhered to itself but not the mandrel. The working length of the balloon was wrapped with two layers of the composite film, as depicted in FIG. 5. The angle was controlled by CADWIND to allow subsequent wraps to lay down next to the previous wrap.

Example 5

Base Layer

For the base layer, the film was positioned by wrapping it around the double stick tape that was earlier applied to the mandrel. In the base layer wrap, both legs were wrapped at an angle (measured from the mandrel axis) of 36 degrees. The shoulders and working length received approximately 2 layers during this wrap, while the legs received approximately 20 layers, as depicted in FIG. 6.

Example 6

Helical 1

For the first helical wrap layer, the film was simply placed onto the previous layers at the approximate angle of wrap. The adherence of the film to the previous layers was enough to secure the film. In the helical 1 wrap configuration, a helical layer was placed on a geodesic (non-slip) path, depositing 2 layers of material at an angle of 6 degrees from the mandrel axis. The wrap extended the axial length of the shoulder, to the start of the legs, as depicted in FIG. 7.

Example 7

Helical 2

For the second Helical wrap layer, the film was simply placed onto the previous layers at the approximate angle of wrap. The adherence of the film to the previous layers was enough to secure the film. In the helical 2 wrap configuration, a helical layer was wrapped on a geodesic (non-slip) path, depositing two layers of material at an angle of 24 degrees from the mandrel axis. This pattern did not extend the entire length of the shoulder so as not to excessively build up the area adjacent to the legs. The wrap opening was 10 mm in diameter and extended 15 mm along the axial length of the shoulder, as depicted in FIG. 8.

Example 8

Helical 3

For the third helical wrap layer, the film was simply placed onto the previous layers at the approximate angle of wrap. The adherence of the film to the previous layers was enough to secure the film. In the helical 3 wrap configuration, a helical layer was wrapped on a geodesic (non-slip) path, depositing two layers of material at an angle of 36 degrees from the mandrel axis. This pattern terminated farther away from the balloon legs than did Helical 2. The wrap opening was 15 mm and extended 10 mm along the axial length of the shoulder, as depicted in FIG. 9.

Example 9

Mandrel Minimization

When the recipe was complete and all wrap layers had been applied, the wrapped mandrel was placed in an oven at 150° C. for 30 minutes. The mandrel was removed from the oven and allowed to cool. The wrapped mandrel was then dissolved by soaking it in water. Water was injected into the wrapped mandrel to aid in the removal of the mandrel. To add robustness to the liquid seal, the ID of the balloon was spray coated with a 5 percent wt PEBAX 2533 (Arkema, Philadelphia, Pa.)/95 percent 1-butynol solution. The coated balloon was allowed to dry under a fume hood, overnight.

The examples produced a 25 mm diameter by 40 mm long non-distensible balloon with a burst pressure of greater than 15 atmospheres.

Example 10

Test Section

The balloon was pre-filled with water before testing commenced. Testing was performed in water at 37° C.

The graph below shows a 15 atmosphere burst pressure design strength and a 30 degree shoulder angle balloon burst tested with a PT3070 Hydraulic Pressure Tester (Interface Associates, Laguna Niguel, Calif.). The mean length change in working length for a 60 degree included angle, 15 atm design was 2 percent, measured with calipers. The balloon wall thickness was 0.35 mm, measured with a drop gauge.

Compliance to Burst Testing 25 mm Diameter×40 mm Working Length Balloon

| Pressure (atm) | Diameter (mm) |
|---|---|
| 1 | 25.37 |
| 2 | 25.64 |
| 3 | 25.71 |
| 4 | 25.77 |
| 5 | 25.84 |
| 6 | 25.87 |
| 7 | 25.94 |
| 8 | 25.99 |
| 9 | 26.05 |
| 10 | 26.09 |
| 11 | 26.11 |
| 12 | 26.16 |
| 13 | 26.26 |
| 14 | 26.33 |
| 15 | 26.47 |
| 16 | 26.58 |
| 17 | 26.74 |
| 18 | 26.97 |

The invention claimed is:

1. A balloon having a longitudinal axis and comprising a base layer, a radial layer, and a helical layer of film, said film does not substantially change length during expansion.

2. The balloon of claim 1 wherein the balloon has an inflation ratio of equal to or greater than 400 percent upon inflation of the balloon.

3. The balloon of claim 1 formed into a non-tubular shape.

4. The balloon of claim 1 wherein the non-tubular shape is a sphere.

5. The balloon of claim 1 wherein the non-tubular shape is a barbell formation.

6. The balloon of claim 1 further comprising a plurality of each base, radial, and helical layers arranged in a configuration to create a high pressure balloon.

7. The balloon of claim 6 wherein transverse strain of the helical layer of film caused by inflation is prevented.

8. The balloon of claim 1 wherein the layers result in an overall balanced force angle upon inflation.

9. The balloon of claim 7 wherein the helical layer of film is formed at the desired final balloon diameter.

10. The balloon of claim 1 wherein the balloon further comprises sections oriented at differing angles to create semi-compliant and non-compliant sections in one balloon.

11. The balloon of claim 1 further comprising an anisotropic film.

12. The balloon of claim 1 wherein the base pass extends from the most distal point of the balloon to the most proximal point of the balloon.

13. The balloon of claim 12 wherein the most distal point is a leg of the balloon.

14. The balloon of claim 13 wherein the base layer further contiguously extends across the opposing balloon shoulder and balloon leg to cover the entire balloon.

15. The balloon of claim 12 wherein the balloon further comprises at least one leg, shoulder, and working length section and the base pass extends contiguously across the at least one leg, shoulder, and working length to tie the sections together.

16. The balloon of claim 15 wherein the base pass forms a seal between the balloon leg and the shoulder.

17. The balloon of claim 16 wherein the base pass seals the leg to a catheter.

18. The balloon of claim 1 formed in a tubular shape.

19. A method of creating a soft, high pressure, large diameter, high expansion ratio balloon with increased burst pressures, comprising:
   a. layering film in essentially longitudinal and essentially helical passes around a mandrel having an outer dimension of the desired final inflated internal diameter of the catheter balloon;
   b. ceasing layering of the mandrel when a final desired strength of the catheter balloon is achieved; and
   c. minimizing the balloon structure diameter to create a soft, high pressure, large diameter.

20. The method of claim 19 wherein the minimizing of the balloon structure is achieved by deflating the mandrel.

21. The method of claim 19 wherein the minimizing of the balloon structure is achieved by dissolving or melting the mandrel.

22. The method of claim 19 wherein the minimizing of the balloon structure is achieved by deflating and removing the mandrel.

23. The method of claim 19 wherein the mandrel is an inflatable bladder.

24. The method of claim 23 wherein the mandrel remains as part of finished device.

25. The method of claim 24 wherein the inflatable bladder is wrapped in a continuous manner.

26. A method of creating a soft, high pressure, large diameter, high expansion ratio balloon with increased burst pressures, comprising:
   a. layering film in helical layers around a mandrel having an outer dimension of the desired final inflated internal diameter of the catheter balloon;
   b. ceasing layering on the mandrel when a final desired strength of the catheter balloon is achieved; and
   c. minimizing the balloon structure diameter to create a soft, high pressure, large diameter, high expansion ratio balloon.

27. The method of claim 26 wherein the minimizing of the balloon structure is achieved by deflating the mandrel.

28. The method of claim 26 wherein the minimizing of the balloon structure is achieved by dissolving or melting the mandrel.

29. The method of claim 26 wherein the minimizing of the balloon structure is achieved by deflating and removing the mandrel.

30. The method of claim 26 wherein the mandrel is an inflatable bladder.

31. The method of claim 26 wherein the mandrel remains as part of finished device.

32. The method of claim 26 further comprising heating the balloon structure to set the layers in place.

33. A non-shortening catheter balloon comprising a balloon having a longitudinal axis said balloon comprising at least one radial layer; at least one base layer; and at least one helical layer.

34. The balloon of claim 33 wherein the at least one radial layer comprises ePTFE and a polyurethane.

35. The balloon of claim 33 wherein the at least one base layer comprises ePTFE and a polyurethane.

36. The balloon of claim 33 wherein the at least one helical layer comprises ePTFE and a polyurethane.

37. A non-shortening catheter balloon comprising a balloon having a longitudinal axis said balloon comprising at least one radial layer; at least one base layer; and three helical layers.

38. A non-shortening catheter balloon of claim 37 wherein the three helical layers are oriented at different angles to the longitudinal axis of the balloon.

39. The balloon of claim 37 wherein the at least one radial layer comprises ePTFE and a polyurethane.

40. The balloon of claim 37 wherein the at least one base layer comprises ePTFE and a polyurethane.

41. The balloon of claim 37 wherein the three helical layers all comprise ePTFE and a polyurethane.

* * * * *